United States Patent
Götz et al.

[19]

[11] Patent Number: 5,831,093

[45] Date of Patent: Nov. 3, 1998

[54] PREPARATION OF N-ARYL- AND N-HETARYLHYDROXYLAMINES

[75] Inventors: Norbert Götz, Worms; Bernd Müller, Frankenthal; Hubert Sauter, Mannheim; Joachim Gebhardt, Wachenheim; Oliver Wagner, Bexbach, all of Germany

[73] Assignee: BASF Aktiengeseschaft, Ludwigshafen, Germany

[21] Appl. No.: 860,671

[22] PCT Filed: Jan. 17, 1996

[86] PCT No.: PCT/EP96/00170

§ 371 Date: Jul. 7, 1997

§ 102(e) Date: Jul. 7, 1997

[87] PCT Pub. No.: WO96/22967

PCT Pub. Date: Aug. 1, 1996

[30] Foreign Application Priority Data

Jan. 28, 1995 [DE] Germany .................. 195 02 700.0

[51] Int. Cl.$^6$ ............... C07D 234/02; C07D 211/72; C07D 249/04; C07D 239/00
[52] U.S. Cl. ............... 544/335; 546/310; 546/312; 546/159; 546/183; 548/255; 548/366.1; 564/300; 564/256
[58] Field of Search ............... 564/300, 256; 546/310, 312, 159, 183; 544/335; 548/255, 366.1

[56] References Cited

U.S. PATENT DOCUMENTS

| | | | |
|---|---|---|---|
| 3,393,237 | 7/1968 | Forman et al. | 564/300 |
| 3,992,395 | 11/1976 | Ludec . | |
| 5,166,435 | 11/1992 | Sharma et al. | 564/300 |
| 5,288,907 | 2/1994 | Sherwin et al. | 564/301 |
| 5,646,327 | 7/1997 | Burns et al. | 558/452 |
| 5,663,433 | 9/1997 | Castelyns et al. | 562/874 |

FOREIGN PATENT DOCUMENTS

| | | |
|---|---|---|
| 147 879 | 7/1985 | European Pat. Off. . |
| 24 55 887 | 11/1974 | Germany . |
| 1092027 | 11/1967 | United Kingdom . |

OTHER PUBLICATIONS

Kosak, John R., Chem. Ind. (Dekker), 1988, 33(Catal. Org. React.), pp. 135–147.

*Primary Examiner*—Deborah C. Lambkin
*Attorney, Agent, or Firm*—Keil & Weinkauf

[57] ABSTRACT

A process for preparing aromatic or heteroaromatic hydroxylamines of the general formula I

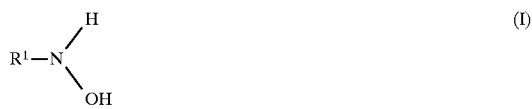

(I)

where $R^1$ is an unsubstituted or substituted aryl radical or an unsubstituted or substituted hetaryl radical from the pyridine or quinoline groups, by hydrogenation of nitro compounds of the general formula II

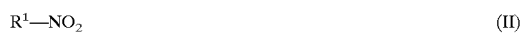

(II)

where $R^1$ has the meaning indicated above, in the presence of a platinum catalyst on an activated carbon support or in the presence of a palladium catalyst doped with sulfur or selenium on an activated carbon support, by carrying out the reaction in the presence of a nitrogen-substituted morpholine compound of the general formula III

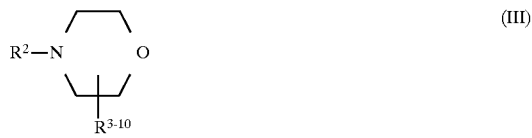

(III)

$R^2$ being alkyl radicals having 1 to 5 carbon atoms and $R^3$ to $R^{10}$ being hydrogen atoms or alkyl radicals having 1 to 5 carbon atoms is described.

8 Claims, No Drawings

PREPARATION OF N-ARYL- AND N-HETARYLHYDROXYLAMINES

The present invention relates to a process for preparing aromatic or heteroaromatic hydroxylamines of the general formula I

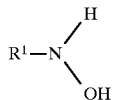

where $R^1$ is an unsubstituted or substituted aryl radical or an unsubstituted or substituted hetaryl radical from the pyridine or quinoline groups, by hydrogenation of nitro compounds of the general formula II

where $R^1$ has the meanings indicated above, in the presence of a platinum catalyst on an activated carbon support or in the presence of a palladium catalyst doped with sulfur or selenium on an activated carbon support, which comprises carrying out the reaction in the presence of a nitrogen-substituted morpholine compound of the general formula III

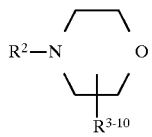

$R^2$ being alkyl radicals having 1 to 5 carbon atoms and $R^3$ to $R^{10}$ being hydrogen atoms or alkyl radicals having 1 to 5 carbon atoms.

The catalytic hydrogenation of aromatic nitro compounds to N-phenylhydroxylamines has been known for a long time (Houben-Weyl, Methoden der Org. Chemie (Methods of Org. Chemistry), Vol. 10/1, pp. 1155–1157; Vol. E 16a, Part 1, pp. 49–53). In comparison to relatively expensive electrochemical reduction and to reduction with metals, such as, for example, with zinc dust, amalgams, inter alia, which have an unfavorable waste material balance, catalytic hydrogenation is the most favorable method from an economic point of view. A problem in this type of reaction is the further reaction to give the aromatic amine, the stable final substance, and the disproportionation of the N-phenylhydroxylamine formed to the corresponding nitroso compounds and anilines. As a result of subsequent reactions, higher molecular weight by-products, such as azoxybenzenes, azobenzenes and hydrazobenzenes, can be formed from these undesirable intermediates and secondary products, which can arise, for example, by condensation of nitrosobenzenes and N-phenylhydroxylamines and further reaction of the azoxybenzenes formed, and under certain circumstances cause substantial losses of yield.

As a rule, Pd or Pt catalysts are recommended for these hydrogenation reactions. In order to obtain yields or selectivities of >50%, according to the present state of knowledge catalyst additives in the form of dimethyl sulfoxide, divalent sulfur compounds or various organic phosphorus compounds are necessary (EP 85890, EP 86363, EP 147879, U.S. Pat. No. 3,694,509, EP 212375).

Using these additives, the improvement in the selectivity is achieved by reducing the reaction rate, which in turn leads to long reaction times. Furthermore, the partial poisoning or inactivation of the catalyst by the additives has the result that the catalyst has usually already lost its activity after one cycle and has to be renewed.

A further method for preparing phenylhydroxylamines is the catalytic hydrogenation of nitroaromatics in the presence of organic nitrogen bases, such as piperidine, pyrrolidine, pyridine, inter alia, which, based on the starting material used, have to be employed in an excess (DE-OS 2 455 238, DE-OS 2 455 887, DE-OS 2 357 370, DE-OS 2 327 412). The yields achievable by this process are, after appropriate working up and purification, 80–85%. It is disadvantageous that using this variant only relatively simple alkyl- and chloronitrobenzenes can be hydrogenated to the corresponding phenylhydroxylamines. Apart from a compound having a 1,3,4-oxadiazole substituent, the hydrogenation of complicated systems by this method is not described.

It is an object of the present invention to make available a process for preparing aromatic and heteroaromatic hydroxylamines which can be carried out simply, is applicable to complicated systems and has a high selectivity and yield.

We have now found that this object is achieved by the process described at the beginning.

It is surprising and was unforeseeable that the partial hydrogenation of aromatic and heteroaromatic nitro compounds to the corresponding hydroxylamines leads to optimum yields and selectivities only in N-alkylmorpholines (N-subst. tetrahydro-1,4-oxazines) as solvents, while according to DE-OS 24 55 238 org. nitrogen bases, such as pyrrolidines, piperidines, anilines or pyridines are recommended as the best solvents for this specific hydrogenation reaction. Comparison experiments (see Examples 1 d–i) show clearly that the N-alkylmorpholines are superior in this specific hydrogenation reaction to other solvent systems, such as pyrrolidines, piperidines, pyridines, inter alia,. In their classification, tertiary amines give better results than secondary amines. The least suitable in this case are primary amines, since as a rule they have selectivities of <80% as a result.

Since the hydroxylamine derivatives obtained as reaction products are very labile compounds which can only be purified with difficulty and decompose relatively rapidly under the action of temperatures of >100° C., it is all the more important that they are obtained by the process according to the invention in high purity and with largely quantitative conversion so that complicated purification by removal of starting material and by-products, such as the corresponding anilines, azoxybenzenes, inter alia, is unnecessary.

Compared with the prior art, the process according to the invention furthermore stands out in that it is very widely applicable. Thus, for example, differently substituted heteroaromatic nitro compounds can be hydrogenated without problems just as selectively as complicated nitroaromatics containing benzylether or oxime ether structures, which as a rule easily undergo undesirable modifications on catalytic hydrogenations (see Example 3).

The nitroaromatics or -heteroaromatics needed as starting materials are readily accessible and their preparation is described widely and in detail (see Houben-Weyl, Vol. 10/1, pp. 463–889 and Vol. E 16 d/Part 1, pp. 255–405).

Suitable compounds for the process according to the invention are both simple nitro compounds, such as, for example, 2-methylnitrobenzene, 2-benzylnitrobenzene, 2,3-dichloronitrobenzene, 2-methyl-3-fluoronitrobenzene, 2-methyl-1-nitronaphthalene, 2-chloro-3-nitropyridine, 2-methyl-8-nitroquinoline, and more complex compounds which additionally have structures sensitive to hydrogenation, such as benzyl ether, oxime ether and keto groups or heteroaromatic substituents.

The catalysts employed according to the process of the invention contain platinum or palladium on a carbon support. When using a palladium catalyst, this must be doped with sulfur or selenium in order to obtain sufficient selectivity (see Example 1c). When used by the process according to the invention without additional doping, platinum gives excellent results. Doping, for example with sulfur, no longer results in any discernible change in selectivity. The catalysts can be filtered off after one reaction cycle and reused in the subsequent batch without noticeable loss of activity. In other processes which proceed using additives such as dimethyl sulfoxide, dimethylaminopyridine or org. phosphorus compounds (EP 86363, EP 85890, EP 147879), as a rule there is a rapid decrease in activity as a result of poisoning of the catalysts. The platinum or palladium content of the catalyst is not critical and can be varied within wide limits.

A content of from 0.1 to 15% by weight, preferably from 0.5 to 10% by weight, based on the support material carbon is expedient. The amount of the platinum or palladium employed is from 0.001 to 1% by weight, preferably from 0.01 to 0.1% by weight, based on the nitro compound. In the preferred embodiment, of a batchwise hydrogenation, the catalyst is employed as a powder. Other supports such as $Al_2O_3$, $SiO_2$, $BaSO_4$, lead to significantly poorer results (see Example 1k). The choice of the right solvents is of crucial importance for the achievement of very good yields, since these affect the activity of the catalysts in such a way that a high selectivity is achieved in the hydrogenation of nitro compounds to the hydroxylamine derivatives.

According to the invention, these solvents are exclusively tert-amines having a morpholine structure, such as, for example, 4-methylmorpholine, 4-ethylmorpholine, 4-propylmorpholine, 4-butylmorpholine, 4-isobutylmorpholine, 4-tertiary-butylmorpholine, 4-pentylmorpholine, 4-isopentylmorpholine, 2,4,6-trimethylmorpholine, 2,3,4,5,6-pentamethylmorpholine, 2,2,4,6,6-pentamethylmorpholine.

As a rule, the tert-amine is employed in an excess, ie. the weight ratio of tert-amine to the nitro compound is greater than 1.

The selected temperature range for the partial hydrogenation is from −20° C. to +100° C., preferably from −5° to +50° C. In order to avoid overhydrogenation, a pressure is established which is between normal pressure and 10 bars overpressure at the temperature at which the hydrogenation proceeds sufficiently rapidly. Normally, the hydrogen is injected into the hydrogenation reactor at normal pressure or slightly elevated pressure. Further solvents or diluents, such as, for example alcohols or ethers, must not be present during the hydrogenation, since they result in a drastic fall in the yield (see Example 1j).

The compounds prepared according to the process of the invention can be converted, as aryl- or hetarylhydroxylamines, into useful substituted aromatics or heteroaromatics using the Bamberger rearrangement (Houben-Weyl, Methoden der Organischen Chemie (Methods of Organic Chemistry), Vol. 10/1, pp. 1249–1251). Furthermore, they are important intermediates for the preparation of active compounds in crop protection agents (WO 93/15046).

In part, novel substances were also prepared by the process according to the invention which could not previously be obtained by other methods.

EXAMPLE 1

Preparation of N-(o-tolyl)hydroxylamine a) A solution of 13.7 g of o-nitrotoluene in 100 ml of N-methylmorpholine and 0.36 g of a catalyst which contained 5% by weight of platinum on carbon (type F 103 RS/W from Degussa) were added to a 250 ml hydrogenation flask having a gas dispersion stirrer. Hydrogen was passed into this mixture with vigorous stirring at from 28° to 30° C. until absorption of hydrogen no longer took place (after about 2 hours and consumption of 4.5 l of hydrogen).

According to HPLC analysis of the crude product, the reaction had proceeded to 96.4% to N-(o-tolyl) hydroxylamine and the remaining 3.6% consisted mainly of unreacted o-nitrotoluene.

After filtering off the catalyst, removing the N-methylmorpholine under reduced pressure and crystallizing the residue from petroleum ether, 11.3 g of N-(o-tolyl) hydroxylamine (m.p. 38°–39° C.) were obtained.

Yield: 92% of theory NMR (DMSO-d6, $\delta$ in ppm): 8.25 (s, 1H), 7.9 (s, 1H), 7.1 (m, 2H), 6.95 (d, 1H), 6.7 (m, 1H)

b) The reaction was carried out in a completely similar manner to a), but N-methylmorpholine was replaced by N-ethylmorpholine. The crude product isolated contained 95.9% N-(o-tolyl)hydroxylamine according to HPLC analysis.

c) The procedure was similar to a), but a catalyst of the composition 5% by weight of palladium and 0.2% by weight of selenium on carbon (type HO-51 from BASF) was employed. The crude product isolated contains 94.2% of N-(o-tolyl)hydroxylamine according to HPLC analysis.

d) The procedure was similar to a), but N-methylmorpholine was replaced by N-methylpiperidine. The crude product isolated contains 86.7% of N-(o-tolyl) hydroxylamine according to HPLC analysis; the remainder was mainly o-toluidine.

f) The reaction was carried out in a similar manner to a), but N-methylmorpholine was replaced by pyridine. The crude product isolated contained 85.6% of N-(o-tolyl) hydroxylamine according to HPLC analysis; the remainder consisted mainly of o-toluidine.

g) The reaction was carried out in a similar manner to a), but N-methylmorpholine was replaced by piperidine. The crude product isolated contained 44.9% of N-(o-tolyl) hydroxylamine and 4.5% of o-toluidine by HPLC analysis; the remainder was mainly the azoxy compound:

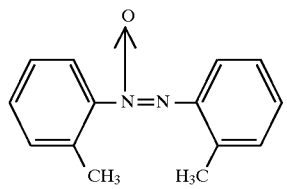

h) The reaction was carried out in a similar manner to a), but N-methylmorpholine was replaced by N,N-dimethylisopropylamine. The crude product isolated contained 62.4% of N-(o-tolyl)hydroxylamine and 9.6% of o-toluidine according to HPLC analysis; the remainder was mainly the azoxy compound:

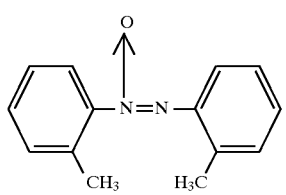

i) The reaction was carried out in a similar manner to a), but N-methylmorpholine was replaced by tert-butylamine. The crude product isolated contained 60.2% of N-(o-tolyl)hydroxylamine and 21.6% of o-toluidine according to HPLC analysis; the remainder was mainly the azoxy compound

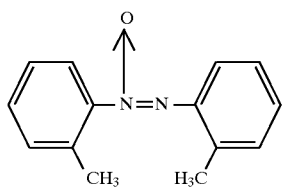

j) The reaction was carried out in a similar manner to a), but the solvent amount of 100 ml of N-methylmorpholine was replaced by a mixture of 70 ml of methanol and 30 ml of N-methylmorpholine. The crude product isolated contained 58.6% of N-(o-tolyl)hydroxylamine and 26.3% of o-toluidine according to HPLC analysis; the remainder still mainly consisted of the starting material o-nitrotoluene.

k) The procedure was similar to a), but a catalyst of the composition 5% platinum on alumina (from Engelhard) was employed. The crude product isolated contained 9.9% of N-(o-tolyl)hydroxylamine and 2.9% of o-toluidine according to HPLC analysis; the remainder still mainly consisted of the starting material o-nitrotoluene.

l) The reaction was carried out in a similar manner to a), but a catalyst of the composition 5% palladium on activated carbon (HO-50 from BASF) was employed. The crude product isolated contained 52.5% of N-(o-tolyl)hydroxylamine according to HPLC analysis; the remainder consisted mainly of o-toluidine.

m) The reaction was carried out in a similar manner to a), but Raney nickel was employed as a catalyst. The crude product isolated contained 58.3% of N-(o-tolyl)hydroxylamine, 16.8% of o-toluidine and 24.9% of o-nitrotoluene according to HPLC analysis.

EXAMPLE 2

Preparation of N-(2,3-dichlorophenyl)hydroxylamine

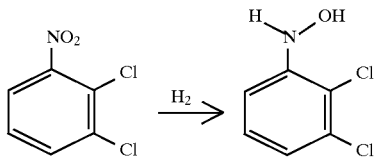

A solution of 134.4 g of 2,3-dichloronitrobenzene in 700 ml of 4-methylmorpholine and 5 g of a catalyst which contained 5% by weight platinum on carbon (type F 103 RS/W from Degussa) was added to a 1.2 l hydrogenation autoclave. Hydrogen was then passed into this mixture with intensive stirring at from 25° to 32° C. and 0.7 bar hydrogen pressure until absorption of hydrogen no longer took place (after about 9 hours and consumption of 32.4 l of hydrogen).

The material discharged from the reaction was filtered off using animal charcoal, and the filtrate was freed from 4-methylmorpholine under reduced pressure (at about 30 mbar), after which the product began to crystallize. After washing twice with 300 ml of cyclohexane each time and then drying, 116.3 g of N-(2,3-dichlorophenyl)hydroxylamine were obtained.

Yield: 93.3% of theory NMR (DMSO-d6, δ in ppm): 8.8 (s, 1H), 8.5 (s, 1H), 7.2 (m, 2H), 7.0 (dd, 1H)

EXAMPLE 3

Reaction

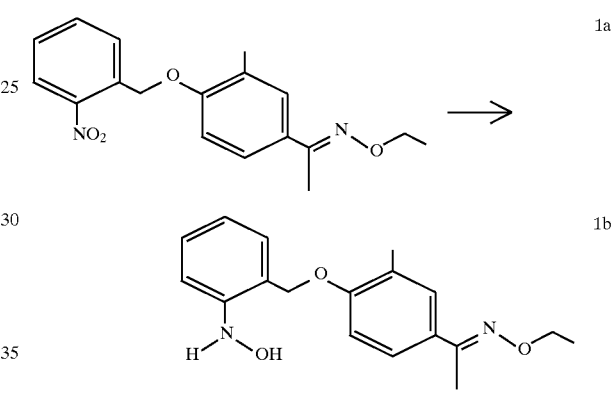

A solution of 410 g of 1a in 2.8 l of 4-methylmorpholine and 12 g of catalyst having the composition 5% by weight of platinum on carbon (type F 103 RS/W from Degussa) was added to a 4 l hydrogenation apparatus. Hydrogen was then passed into this mixture with intensive stirring at from 24° to 29° C. and 0.1 bar hydrogen pressure until absorption of hydrogen no longer took place (after about 4 h and consumption of 57.5 l of hydrogen).

The material discharged from the reaction was filtered off with animal charcoal, the filtrate was concentrated on a rotary evaporator (under reduced pressure at 25–30 mbar and a bath temperature of 65° C.) and the residue was crystallized by treatment with 1.2 l of pentane.

The crystals were filtered off, washed with a little pentane and dried. 359.2 g of compound 1b were obtained, corresponding to a yield of 91.5 % of theory.

NMR (DMSO-d6, δ in ppm): 8.45 (s, 1H); 8.1 (s, 1H), 7.5 (s, 1H), 7.45 (d, 1H), 7.25 (m, 3H), 7.0 (d, 1H), 6.85 (m, 1H), 5.05 (s, 2H), 4.15 (q, 2H), 2.25 (s, 3H), 2.15 (s, 3H), 1.25 (t, 3H)

In a similar manner to Examples 1a, 2 and 3, the following compounds were prepared which show the breadth of application of the process according to the invention.

| Structure | NMR data (DMSO-d$_6$, δ in ppm) |
|---|---|
| 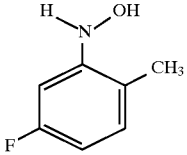 | 8.45(s, 1H), 8.2(s, 1H), 7.95(t, 1H) 6.8(dd, 1H), 6.45(dt, 1H), 2.0(s, 3H) |
| 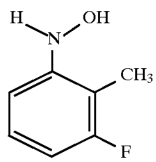 | 8.4(s, 1H), 8.15(s, 1H), 7.0(m, 2H) 6.55(t, 1H), 2.0(s, 3H) |
| 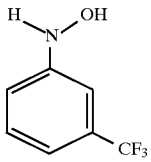 | 8.7(s, broad, 2H), 7.4(t, 1H), 7.05(m, 3H) |
| 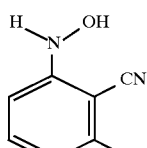 | 8.05(s, broad, 2H), 7.1(t, 1H), 6.95(d, 1H), 6.55(d, 1H) |
| 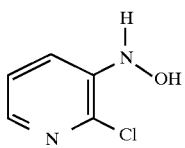 | 8.8(s, broad, 1H), 8.5(s, 1H), 7.8(s, broad, 1H), 7.5(d, 1H), 7.4(d, broad, 1H) |
| 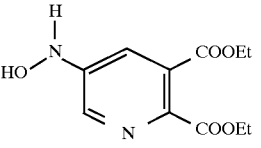 | |
| 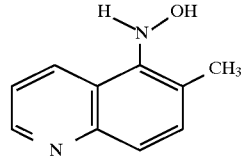 | 8.85(m, 2H), 7.75(s, very broad, 1H), 8.0(s, very broad, 1H), 7.7(d, 1H), 7.5(m, 2H), 2.5(s, 3H) |
| 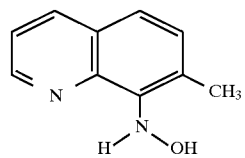 | 8.85(s, 1H), 8.7(s, 1H), 8.3(d, 1H), 7.5(m, 4H), 2.6(s, 3H) |
| 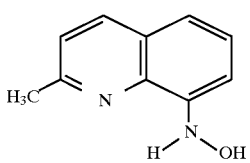 | 8.75(s, 1H), 8.65(s, 1H), 8.1(d, 1H), 7.3(m, 4H), 2.6(s, 3H) |

-continued
| Structure | NMR data (DMSO-d$_6$, δ in ppm) |
|---|---|
|  | |
| 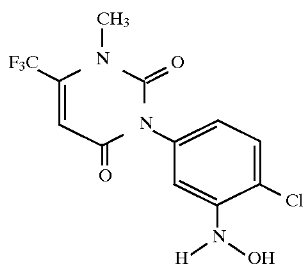 | 8.4(s, very broad, 2H), 7.35(d, 1H), 7.1(d, 1H), 6.7(dd, 1H), 6.45(s, 1H), 3.4(s, 3H) |
| 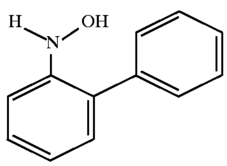 | 7.4(m, 5H), 7.3(m, 2H), 7.25(m, 2H), 7.05(d, 1H), 6.9(dt, 1H) |
| 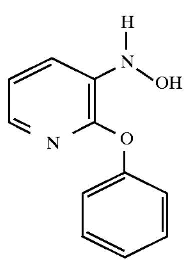 | 8.6(s, 1H), 8.5(s, 1H), 7.4(m, 4H), 7.1(m, 4H) |
| 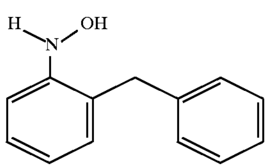 | 8.3(s, 1H), 8.05(s, 1H), 7.2(m, 7H), 6.9(d, 1H), 6.7(m, 1H), 3.8(s, 2H) |
|  | |
| 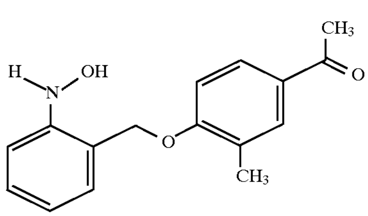 | 8.5(s, broad, 1H), 8.15(s, 1H), 7.85(m, 2H), 7.3(m, 3H), 7.1(d, 1H), 6.9(m, 1H), 5.15(s, 2H), 2.5(s, 3H), 2.25(s, 3H) |

| Structure | NMR data (DMSO-d$_6$, δ in ppm) |
|---|---|
| (structure: 4-fluoro-2-[(2,5-dimethylphenoxy)methyl]-N-hydroxyaniline) | |
| (structure: 4-fluoro-2-[[4-(1-methoxyiminoethyl)-2-methylphenoxy]methyl]-N-hydroxyaniline) | 8.5(s, 1H), 8.1(s, 1H), 7.5(s, 1H), 7.45(d, 1H), 7.1(m, 4H), 5.1(s, 2H), 3.9(s, 3H), 2.25(s, 3H), 2.1(s, 3H) |
| (structure: N-tert-butyl-5-(hydroxyamino)pyridine-2,3-dicarboximide) | 9.6(s, very broad, 2H), 8.4(d, 1H), 7.5(d, 1H), 1.6(s, 9H) |
| (structure: N-hydroxy-4-chloroaniline) | 8.4(s, very broad, 2H), 7.2(d, 2H), 6.9(d, 2H) |
| (structure: 2-[(2,5-dimethylphenoxy)methyl]-N-hydroxyaniline) | 8.5(s, very broad, 1H), 8.0(s, 1H), 7.35(d, 1H), 7.25(m, 2H), 7.0(d, 1H), 6.85(m, 2H), 6.65(d, 1H), 5.0(s, 2H), 2.3(s, 3H), 2.2(s, 3H) |
| (structure: 3-(hydroxyamino)-2-methylpyridine) | 8.6(s, very broad, 1H), 8.2(s, 1H), 7.9(d, 1H), 7.4(d, 1H), 7.1(dd, 1H), 2.3(s, 3H) |
| (structure: bis-aryloxy diimine compound) | |
| (structure: methyl 2-[2-[[3-(hydroxyamino)phenoxy]methyl]phenyl]-2-(methoxyimino)acetate) | 8.3(s, very broad, 2H), 7.55(m, 1H), 7.4(m, 2H), 7.25(m, 1H), 7.05(t, 1H), 6.4(m, 2H), 6.3(d, broad, 1H), 4.85(s, 2H), 3.9(s, 3H), 3.75(s, 3H) |

-continued

| Structure | NMR data (DMSO-d$_6$, δ in ppm) |
|---|---|
| (structure) | 9.1(s, 1H), 8.3(s, 1H), 7.8(d, 2H), 7.55(t, 2H), 7.3(m, 5H), 6.8(dt, 1H), 5.35(s, 2H) |
| (structure) | |
| (structure) | |
| (structure) | |
| (structure) | |
| (structure) | |

| Structure | NMR data (DMSO-d$_6$, δ in ppm) |
|---|---|
| | |

-continued

| Structure | NMR data (DMSO-d$_6$, δ in ppm) |
|---|---|
| | |
| | |
| | |
| 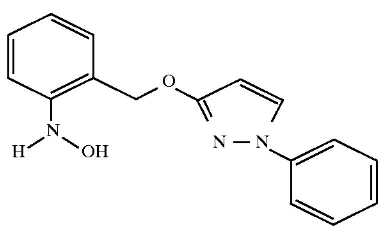 | 8.4(s, 1H), 8.35(d, 1H), 8.2(s, 1H), 7.75(d, 2H), 7.5(t, 2H), 7.3(d, 1H) 7.2(m, 3H), 6.8(dt, 1H), 6.1(d, 1H), 5.2(s, 2H) |
| | |
| | |
| | |

We claim:
1. A process for preparing aromatic or hetaromatic hydroxylamines of the formula I

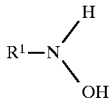 (I)

where $R^1$ is an unsubstituted or substituted aryl radical or an unsubstituted or substituted hetaryl radical selected from the group consisting of pyridine and quinoline, by hydrogenation of nitro compounds of the formula II

 (II)

where $R^1$ has the meanings indicated above, in the presence of a platinum catalyst on an activated carbon support or in the presence of a palladium catalyst doped with sulfur or selenium on an activated carbon support, which comprises carrying out the reaction in the presence of a nitrogen-substituted morpholine compound of the formula III

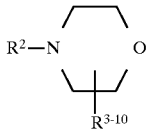 (III)

$R^2$ being alkyl radicals having 1 to 5 carbon atoms and $R^3$ to $R^{10}$ being hydrogen atoms or alkyl radicals having 1 to 5 carbon atoms.

2. The process of claim 1, wherein $R^1$ is a substituted aryl radical or hetaryl radical which can carry 1 to 3 substituents $R^{11}$, $R^{12}$ and $R^{13}$, it being possible for $R^{11}$, $R^{12}$ and $R^{13}$ to be identical or different and to have the following meanings:
hydrogen, halogen, $C_1$–$C_4$-alkyl, halo-($C_1$–$C_4$)-alkyl, ($C_1$–$C_4$)-alkoxy, ha-lo-($C_1$–$C_4$)-alkoxy, $C_1$–$C_4$-alkylthio, ($C_1$–$C_4$)-alkylcarbonyl, ($C_1$–$C_4$)-alkyl-($CR^{14}$=N—O—($C_1$–$C_4$)-alkyl), ($C_1$–$C_4$)-alkoxycarbonyl, ($C_1$–$C_4$)-alkylaminocarbonyl, ($C_1$–$C_4$)-dialkylaminocarbonyl, ($C_1$–$C_4$)-alkylcarbonylamino, ($C_1$–$C_4$)-alkylcarbonyl-($C_1$–$C_4$)-alkylamino, —$CH_2O$—N=C($R^{15}$)—C($R^{16}$)=N—O—$R^{17}$, cyano or the group A—B,
A being —O—, —S—, —O—$CH_2$—, —$CH_2$—O—, —S—$CH_2$—, —$CH_2$—S—, —$CH_2$—O—CO—, —$CH_2$—N($R^{18}$)—, —CH=CH—, —CH=N—O—, —$CH_2$—O—N=C($R^{15}$)— or a single bond and B being phenyl, naphthyl, pyridinyl, pyrazinyl, pyrimidinyl, pyridazinyl, pyrazolyl, imidazolyl, oxazolyl, isoxazolyl, thiazolyl, isothiazolyl, 1,2,4-triazolyl, 1,2,3-triazolyl, furanyl, thienyl, pyrrolyl or $C_3$–$C_7$-cycloalkyl, it being possible for B to be substituted by 1–3 substituents $R^{19}$, $R^{14}$ and $R^{18}$ are independently of one another $C_1$–$C_4$-alkyl, $C_2$–$C_4$-alkenyl, $C_2$–$C_4$-alkynyl or hydrogen, $R^{15}$ and $R^{17}$ are hydrogen, $C_1$–$C_4$-alkyl, $C_1$–$C_4$-alkoxy, cyano, $C_1$–$C_4$-alkylthio, halogen, cyclopropyl or trifluoromethyl and $R^{19}$ is hydrogen, halogen, $C_1$–$C_4$-alkyl, halo-($C_1$–$C_4$)-alkyl, ($C_1$–$C_4$)-alkoxy, halo-($C_1$–$C_4$)-alkoxy, $C_1$–$C_4$-alkylthio, ($C_1$–$C_4$)-alkylcarbonyl, ($C_1$–$C_4$)-alkyl-($CR^{14}$=N—O—($C_1$–$C_4$)-alkyl), ($C_1$–$C_4$)-alkoxycarbonyl, ($C_1$–$C_4$)-alkylaminocarbonyl, ($C_1$–$C_4$)-dialkylaminocarbonyl, ($C_1$–$C_4$)-alkylcarbonylamino, ($C_1$–$C_4$)-alkylcarbonyl-($C_1$–$C_4$)-alkylamino, or cyano $R^{16}$ is $C_1$–$C_4$-alkyl, $C_3$–$C_6$-cycloalkyl, phenyl, hetaryl or heterocyclyl.

3. The process of claim 1, wherein the morpholine compound of the formula III employed is 4-methylmorpholine, 4-ethylmorpholine, 4-propylmorpholine, 4-butylmorpholine, 4-isobutylmorpholine, 4-tertiarybutylmorpholine, 4-pentylmorpholine, 4-isopentylmorpholine, 2,4,6-trimethylmorpholine, 2,3,4,5,6-pentamethylmorpholine or 2,2,4,6,6-pentamethylmorpholine.

4. The process of claim 1, wherein the weight ratio of morpholine compound to nitro compound is greater than 1.

5. The process of claim 1, wherein the platinum catalyst or the palladium catalyst is used in an amount from 0.1 to 15% by weight, based on the activated carbon support.

6. The process of claim 1, wherein the platinum catalyst or the palladium catalyst is used in an amount from 0.001 to 1.0% by weight of platinum or palladium, based on the nitro compound.

7. The process of claim 1, wherein the hydrogenation is carried out at from −20° C. to 100° C.

8. The process of claim 1, wherein the hydrogenation is carried out at a pressure from normal pressure to 10 bars overpressure.

* * * * *